(12) United States Patent
Croker et al.

(10) Patent No.: US 7,572,643 B2
(45) Date of Patent: Aug. 11, 2009

(54) NANOPARTICLE COMPOSITE-COATED GLASS MICROSPHERES FOR USE IN BIOASSAYS

(75) Inventors: Kevin Michael Croker, Hockessin, DE (US); Michael B. Damore, Wilmington, DE (US); Kostantinos Kourtakis, Media, PA (US); Michael P. Perry, Landenberg, PA (US); James M. Prober, Wilmington, DE (US); Paul Douglas Stull, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 345 days.

(21) Appl. No.: 11/284,155

(22) Filed: Nov. 21, 2005

(65) Prior Publication Data

US 2007/0117224 A1  May 24, 2007

(51) Int. Cl.
  *G01N 33/551*  (2006.01)
  *G01N 33/552*  (2006.01)
  *G01N 33/553*  (2006.01)
(52) U.S. Cl. .............................. 436/524; 435/5; 435/6; 435/7.2; 435/7.21; 435/7.32; 435/7.5; 436/525; 436/527
(58) Field of Classification Search .................. None
  See application file for complete search history.

(56) References Cited

U.S. PATENT DOCUMENTS 6,268,222 B1 * 7/2001 Chandler et al. ............ 436/523

2004/0258611 A1  12/2004  Barrow et al.
2005/0019842 A1   1/2005  Prober et al.

FOREIGN PATENT DOCUMENTS

| EP | 0 246 757 A2 | 11/1987 |
| JP | 02097581 A | 4/1990 |
| KR | 10-0467770 B | 1/2005 |
| WO | WO 01/46471 A1 | 6/2001 |

OTHER PUBLICATIONS

U.S. Appl. No. 10/702,320, filed Nov. 5, 2003, Prober et al.
Inorganic Colloid Chemistry, vols. 1, 2 and 3, J. Wiley and Son, Inc., New York, NY, 1935 (Book Not Supplied).
Bradley et al., Metal Alkoxides, Academic Press, New York, NY, 1978 (Book Not Supplied).
Emanuele Ostuni et al., A Survey of Structure-Proeprty Relationships of Surfaces That Resist the Adsorption of Protein, Langmuir, vol. 17:5605-5620, 2001.
Danhua Wang et al., Novel Benzo-15-Crown-5 Sol-Gel Coating for Solid-Phase, Journal of Chromatography A, vol. 1005:1-12, 2003.

(Continued)

*Primary Examiner*—Christopher L Chin (57) ABSTRACT

A microsphere for use in a bioassay comprising a glass core coated with a nanoparticle composite comprising a bioactive probe is provided. The nanoparticle composite coating enhances the density of bioprobe loading on the surface of the microspheres, resulting in enhanced dynamic range and sensitivity in bioassays. The particle may be used in detection systems where resonant light scattering properties of the particle are useful.

14 Claims, 2 Drawing Sheets

OTHER PUBLICATIONS

Zhihong Wang et al., Dense PZT Thick Films Derived From Sol-Gel Based Nanocomposite Process, Materials Science and Engineering, vol. B99:56-62, 2003.

Y. Castro et al., Coatings Produced by Electrophoretic Deposition From Nano-Particulate Silica Sol-Gel Suspensions, Surface and Coatings Technology, vol. 182:199-203, 2004.

Christopher J. Larson et al., A High-Capacity Column for Affinity Purification of Sequence-Specific DNA-Binding Proteins, Nucleic Acids Research, vol. 20(13):3525, 1992.

James T. Kadonaga, Purification of Sequence-Specific Binding Proteins by DNA Affinity Chromatography, Methods in Enzymology, vol. 208:10-23, 1991.

Rolf Lohrmann et al., New Solid Supports for DNA Synthesis, Fourth Annual Congress for Recombinant DNA Research, p. 122.

H. Schmidt et al., The Sol-Gel Process as a Basic Technology for Nanoparticle-Dispersed Inorganic-Organic Composites, Journal of Sol-Gel Science and Technology, vol. 19:39-51, 2000.

Kulwinder Flora et al., Comparison of Formats for the Development of Fiber-Optic Biosensors Utilizing Sol-Gel Derived Materials Entrapping Fluorescently-Labelled Protein, Analyst, vol. 124:1455-1462, 1999.

Sarita V. Malik et al., Immobilization of Porcine Pancreas Lipase on Zirconia Coated Alkylamine Glass Using Glutaraldehyde, Indian Journal of Chemical Technology, vol. 7:64-67, 2000.

G. Carturan, Preparation of Supports for Catalysis by the "Gel Route", Journal of Non-Crystalline Solids, vol. 63:273-281, 1984.

A. Peter Jardine, Synthesis and Characterization of PZT Coatings on Glass Microspheres, Mat. Res. Soc. Symp. Proc., vol. 372:151-154, 1995.

M. Haraguchi et al., Fabrication and Optical Characterization of a TiO2 Thin Film on a Silica Microsphere, Surface Science, vol. 548:59-66, 2004.

Joanne D. Andreadis et al., Use of Immobilized PCR Primers to Generate Covalently Immobilized DNAs for In Vitro Transcription/Translation Reactions, Nucleic Acids Research, vol. 28(2):ii-vii, 2000.

Toribio & Ovejero, J. Mat. Eng. Perform. 9:272-79 (2000).

* cited by examiner

NANOPARTICLE COMPOSITE-COATED GLASS MICROSPHERES FOR USE IN BIOASSAYS

FIELD OF THE INVENTION

The invention relates to glass microspheres for use in bioassays. Specifically, glass microspheres are provided having a specific nanoparticle composite coating composition that enhances the density of bioprobe loading on the surface of the microspheres.

BACKGROUND OF THE INVENTION

There is a need for highly sensitive diagnostic tools for the detection of biological analytes in the pharmaceutical, diagnostics, agriculture, veterinary and health care industries. The use of resonant light scattering as an analytical method in these areas is an emerging technology that is ripe for further development. A key component of such methods is particles or microspheres having unique resonant light scattering properties.

The use of resonant light scattering as an analytical method for determining a particle's identity and the presence and optionally, the concentration of one or more target analytes has been described (Prober et al., copending and commonly owned U.S. patent application Ser. No. 10/702,320 and U.S. Patent Application Publication No. 2005/0019842). In that method, a microparticle is irradiated with light of a given wavelength and the resonant light scattering from the microparticle is detected. As the incident wavelength is scanned (i.e., varied over an analytical wavelength range) a scattering pattern or scattering spectrum as a function of wavelength results. Each particle has a distinct resonance light scattering spectrum that can be used to identify the particle. The presence and optionally the concentration of a target analyte can be determined from the shift in the resonance light scattering spectrum that occurs when the analyte binds to a capture probe attached to the surface of the particle. The magnitude of the shift is related to the concentration of the analyte in the solution.

A key aspect of the above described method is the nature of the particle, and the ability of the particle to both bind a bio-analyte while at the same time retaining light scattering properties. The dynamic range and the sensitivity of the method are limited by the amount of bioprobe that can be attached to the surface of the particle. Modifications of the particle that could enhance the dynamic range and the sensitivity of the resonant light scattering measurements would be an advance in the art. One tool for such a modification encompasses the use of nanoparticle composite coatings for the surface modification of these particles.

The use of sol-gel materials to modify particle or nanoparticle surfaces is known (see review by Schmidt et al., *Journal of Sol-Gel Science and Technology* (2000), 19(1/2/3), 39-51). This technology has been applied in processes for the analysis of bio-analytes. For example, Flora et al., (*Analyst* (Cambridge, United Kingdom) (1999), 124(10), 1455-1462) teach the use of sol-gel particles for the adsorption of proteins for fiber-optic analysis. Similarly, glass beads comprising coatings of zirconia (Malik et al., (*Indian Journal of Chemical Technology* (2000), 7(2), 64-67) or alkoxysilane (Kuramoto et al, JP02097581) have been prepared and used to immobilize enzymes. Additionally, colloidal sol-gel composites have been coated on the surface of $SiO_2$ particulate substrates to modify light transmission properties of the substrate (Garvey et al., EP246757), and non-colloidal sol-gel coatings have been applied to glass beads to modify the refractive indices of the beads (Jun et al., KR2002017667), by using the so-called sol-gel reaction. Additional modification of glass surfaces with sol-gels have been reported, see for example Carturan et al., (*Journal of Non-Crystalline Solids* (1984), 63(1-2), 273-81) describing coating glass beads with thin layer porous oxides comprised of $SiO_2/Al_2O_3/Na_2O$; and Jardine, A. Peter, (*Materials Research Society Symposium Proceedings* (1995), 37, (*Hollow and Solid Sphere and Microspheres: Science and Technology Associated with Their Fabrication and Application*), describing the synthesis of $Pb(Ti,Zr)O_3$ (PZT) coatings on glass microspheres using sol-gel techniques; and Haraguchi et al. (*Surface Science* (2004), 548(1-3), 59-66), reporting the fabrication of a uniform $TiO_2$ thin film on $SiO_2$ microspheres.

Although the above described particle modifications are useful, none of the disclosures teach a particle having enhanced binding for bio-analytes or the compositions needed for detection by resonant light scattering means. Applicants provide herein a new glass particle having been modified with a nanoparticle composite coating that provides for greater density of bioprobe loading on the surface of the particle, resulting in enhanced dynamic range and sensitivity in resonant light scattering assays.

SUMMARY OF THE INVENTION

The invention provides a microsphere for use in a bioassay. Accordingly, the invention provides a microsphere for use in a bioassay comprising a glass core coated with a nanoparticle composite coating comprising a bioactive probe.

In one embodiment, the invention provides a microsphere for use in a bioassay comprising a glass core coated with a nanoparticle composite coating comprising a bioactive probe, wherein the nanoparticle composite coating comprises:

a) a colloidal oxide of an element selected from the group consisting of silicon, zirconium, aluminum, titanium, cerium, antimony, and mixtures thereof, wherein the colloidal oxide has a particle size of about 2 nanometers to about 100 nanometers; and b) an oxide or oxyhydroxide of an element selected from the group consisting of: silicon, zirconium, aluminum, titanium, tantalum, niobium, and mixtures thereof.

In another embodiment, the invention provides a method for the detection of analyte binding to a nanoparticle composite-coated microsphere comprising:

a) providing a light scanning source which produces light over an analytical wavelength range;

b) providing at least one nanoparticle composite coated microsphere comprising a glass core coated with a nanoparticle composite comprising a bioactive probe, wherein the bioactive probe has affinity for at least one analyte;

c) optionally scanning the nanoparticle composite coated microsphere of (b) one or more times over the analytical wavelength range to produce at least one first reference resonant light scattering spectrum for the nanoparticle composite coated microsphere of (b);

d) contacting the nanoparticle composite coated microsphere of (c) with a sample suspected of containing at least one analyte where, if the analyte is present, binding occurs between the at least one bioactive probe and the at least one analyte;

e) scanning the nanoparticle composite coated microsphere of (d) one or more times over the analytical wavelength range to produce at least one second binding resonant light scattering spectrum for each nanoparticle composite coated microsphere of (d); and f) detecting binding of the at least one analyte to the at least one bioactive probe by comparing the differences between the resonant light scattering spectra selected from the group consisting of: any of the at least one first reference light scattering spectrum and any of the at least one second light scattering spectrum.

BRIEF DESCRIPTION OF THE FIGURES

The invention can be more fully understood from the following detailed description and figures, which form a part of this application.

DETAILED DESCRIPTION OF THE INVENTION

The invention provides a microsphere for use in a bioassay comprising a glass core coated with a nanoparticle composite comprising a bioactive probe. The nanoparticle composite coating enhances the density of bioprobe loading on the surface of the microspheres, thereby enhancing the dynamic range and the sensitivity in resonant light scattering assays.

The nanoparticle composite-coated glass microspheres of the invention have application in methods of specific analyte detection and particle identification, which are based on the measurement of resonant light scattering. The methods are capable of parallel analysis with high multiplicity.

The following definitions and abbreviations are to be used for the interpretation of the claims and the specification.

The terms "particle", "microparticle", "bead", "microbead", "microsphere", and grammatical equivalents refer to small discrete particles, substantially spherical in shape, having a diameter of about 10 micrometers to about 100 micrometers, preferably about 10 micrometers to about 75 micrometers, more preferably about 10 micrometers to about 50 micrometers.

The term "bioactive" when referring to a capture probe refers to a capture probe that is able to participate in biological interactions, such as interactions between members of binding pairs.

The terms "capture probe", "probe", "binding agent", "bioactive agent", "binding ligand", "bioprobe", or grammatical equivalents, refer to any chemical or biological structure or moiety, for example protein, polypeptide, polynucleotide, antibody or antibody fragment, biological cells, microorganisms, cellular organelles, cell membrane fragments, bacteriophage, bacteriophage fragments, whole viruses, viral fragments, organic ligand, organometallic ligand, and the like that may be used to bind either non-specifically to multiple analytes, or preferentially, to a specific analyte or group of analytes in a sample.

The term "binding-pair" includes any of the class of immune-type binding-pairs, such as, antigen/antibody, antigen/antibody fragment, or hapten/anti-hapten systems; and also any of the class of nonimmune-type binding-pairs, such as biotin/avidin, biotin/streptavidin, folic acid/folate binding protein, hormone/hormone receptor, lectin/specific carbohydrate, enzyme/cofactor, enzyme/substrate, enzyme/inhibitor, or vitamin B12/intrinsic factor. They also include complementary nucleic acid fragments (including DNA sequences, RNA sequences, and peptide nucleic acid sequences), as well as Protein A/antibody or Protein G/antibody, and polynucleotide/polynucleotide binding protein. Binding pairs may also include members that form covalent bonds, such as, sulfhydryl reactive groups including maleimides and haloacetyl derivatives; amine reactive groups such as isothiocyanates, succinimidyl esters, carbodiimides, and sulfonyl halides; and carbodiimide reactive groups such as carboxyl and amino groups.

The terms "protein", "peptide", "polypeptide" and "oligopeptide" are herein used interchangeably to refer to two or more covalently linked, naturally occurring or synthetically manufactured amino acids.

The term "atom %" as used herein, refers to the percentage of silicon atoms in the glass compositions of the invention relative to the total number of cationic atoms (i.e., excluding oxygen and other anions) in the composition.

The terms "analyte" or "bio-analyte" refer to a substance to be detected or assayed using the microspheres of the present invention. Typical analytes may include, but are not limited to, proteins, peptides, nucleic acids, peptide nucleic acids, antibodies, receptors, molecules, biological cells, microorganisms, cellular organelles, cell membrane fragments, bacteriophage, bacteriophage fragments, whole viruses, viral fragments, and one member of a binding pair.

The terms "target" and "target analyte" refer to the analyte targeted by the assay. Sources of targets will typically be isolated from organisms and pathogens such as viruses and bacteria or from an individual or individuals, including but not limited to, for example, skin, plasma, serum, spinal fluid, lymph fluid, synovial fluid, urine, tears, blood cells, organs, tumors, and also to samples of in vitro cell culture constituents (including but not limited to conditioned medium resulting from the growth of cells in cell culture medium, recombinant cells and cell components). Additionally, targets may be from synthetic sources.

The term "resonant light scattering spectrum" refers to a plot of resonant light scattering intensity as a function of wavelength obtained by scanning the glass microspheres of the invention over an analytical wavelength range and measuring the resulting resonant light scattering signal.

The terms "spectral features", "optical resonance structures", "identification features", "scattering resonances", and "resonant light scattering signatures" are used interchangeably herein to refer to features in the resonant light scattering spectrum that may be used for particle identification, including, but not limited to peak location, peak width, peak order, periods between peaks of different orders, and polarization-dependent spectral properties.

The phrase "richness of spectral features" when used in relation to a resonant light scattering spectrum, refers to a spectrum that has a multitude of spectral features that may be used for particle identification.

The term "analytical wavelength range" refers to a wavelength window over which the microspheres of the present invention are scanned to produce resonant light scattering signatures. The window typically has a span of about 1 to about 20 nanometers over the optical wavelengths from about 275 to about 1900 nanometers, preferably from about 600 to about 1650 nanometers. More preferably, the analytical wavelength range spans a range of 10 nanometers from about 770 to about 780 nanometers. It is contemplated that a number of scans of the particles of the invention may be made during the process of identifying an analyte or detecting analyte binding, however each of these scans will be over an "analytical wavelength range" although that range may differ from scan to scan depending on the specific object of the assay.

The term "light scanning source" refers to a source of light whose wavelength may be varied over the analytical wavelength range. Light scanning sources include sources that produce light that may be varied over the analytical wavelength range, such as scanning diode lasers and tunable dye lasers, and polychromatic sources which produce light having a range of wavelengths, such as light-emitting diodes, lamps and the like, used in conjunction with a wavelength-selecting means.

The term "reference resonant light scattering spectrum" refers to the resonant light scattering spectrum that is produced by scanning the microspheres of the present invention over the analytical wavelength range after the capture probe has been applied to the particles or in the case of detection of analyte dissociation from the capture probe, after the analyte has bound to the capture probe. The reference resonant light scattering spectrum may be used to identify the particles and the probes attached thereto and may serve as a baseline for the detection of analyte binding. A number of reference resonant spectra may be obtained by scanning the particles at different times.

The term "binding resonant light scattering spectrum" refers to the resonant light scattering spectrum that is produced by scanning the microspheres of the present invention over the analytical wavelength range after the microspheres are contacted with the analyte. A series of binding resonant light scattering spectra may be obtained to follow the binding in real time. The determination of binding is done by comparing either any one of the binding resonant light scattering spectra to any one of the reference resonant light scattering spectra or anyone of the plurality of binding resonant light scattering spectra with a previous binding resonant light scattering spectra in the series.

The invention provides a microsphere for use in a bioassay comprising a glass core coated with a nanoparticle composite comprising a bioactive probe. A key component of the invention is the construction of a three dimensional nanocomposite structure that surrounds the glass core. It is postulated that the three dimensional nature and the porosity of the structure allows for a higher volumetric density of probes that can bind to target molecules. The higher density of probes enables a greater number of target molecules to bind to the probe, which causes a proportionally larger change in refractive index at the surface of the microsphere. This results in a larger response in the resonant light scattering spectrum by inducing a greater shift in the wavelength of one or more resonance peaks. Additionally, the sensitivity towards low concentrations of analyte should be improved as a consequence of the improved volumetric density of probes.

Glass Cores

For use in the invention, the glass core is a glass microbead that is substantially spherical in shape, and has a diameter of about 10 micrometers to about 100 micrometers, preferably about 10 micrometers to about 75 micrometers, more preferably about 10 micrometers to about 50 micrometers. The term "substantially spherical", as used herein, means that the shape of the glass core does not deviate from a perfect sphere by more than about 10%. The refractive index of the glass core is about 1.4 to about 2.1.

Suitable glass cores for use in the invention are comprised of materials including, but not limited to, oxides of barium, bismuth, titanium, iron, sodium, calcium, boron, niobium, tantalum, lanthanum, silicon, strontium, chromium, and tungsten. Barium titanium silicon oxide glasses have been found to be particularly useful in resonant light scattering methods for identification of the microspheres as well as for analyte detection because of the richness of spectral features in their light scattering spectra. Additionally, glass cores having a composition comprised of calcium, titanium, silicon and oxygen, and glass cores having a composition comprising a silicon content of at least about 50 atom %, for example, borosilicate glasses, are particularly useful for high sensitivity detection.

In one embodiment, the glass core has a composition of:

wherein $0.6>y>0.1$; $0.6>y'>0.05$; $0.6>y''\geq0$; $0.4>y'''\geq0$; $x=y+y'+y''+y'''$; A is any of, or a combination of Na, Fe, Sr, and Zr; $0.01>a\geq0$, and $2\geq z\geq0.5$.

In another embodiment, the glass core has a composition of:

wherein $x=y+y'+y''+y'''$; $y=0.394$; $y'=0.113$; $y''=0.134$; $y'''=0.066$; $a=0.005$; $2\geq z\geq0.5$; and wherein A is a combination of Fe, Sr, Na, and Zr.

In another embodiment, the glass core has a composition of:

wherein $0.5>y>0.1$; $0.6>y'>0.05$; $0.6>y''>0.04$; $0.4>y'''\geq0$; $0.3>y''''\geq0$; $x=y+y'+y''+y'''+y''''$; where A is any of, or a combination of Cr, Fe, W, Na and Zr; $0.01>a\geq0$; and $3\geq z\geq0.5$.

In another embodiment, the glass core has a composition of:

wherein $y=0.171$, $y'=0.401$, $y''=0.044$, $y'''=0.0614$, $y''''=0.0194$, $x=y+y'+y''+y'''+y''''$; $a=0.0044$; $3\geq z\geq0.5$; and A is a combination of Cr, Fe, W, Na, and Zr.

In another embodiment, the glass core has a composition comprised of calcium, titanium, silicon and oxygen, wherein the calcium, titanium, and silicon content is given by:

and wherein x and y are independently equal to 0.2 to 0.5, preferably between 0.3 and 0.4. An example of glass compositions of this type is:

wherein x and y are independently equal to 0.2 to 0.5, preferably between 0.3 and 0.4.

In another embodiment, the glass core has a composition comprising a silicon content of at least about 50 atom %, for example, borosilicate glasses. An exemplary glass composition of this type is:

wherein $x=y+y'+y''$, provided that x is less than or equal to 0.5; $0.5>y\geq0.1$; $0.1\geq y'\geq0$, $0.1\geq y''\geq0$; A is any of, or a combination of Fe, Ca, and K; $0.1>a\geq0$; and $1.5\geq z\geq0.5$.

In another embodiment, the glass core has a composition of:

wherein x=y+y'+y"; y=0.213; y'=0.0258; and y"=0.035; a=0.002; A is any of, or a combination of Fe, Ca, and K; and 1.5≧z≧0.5.

In another embodiment, the glass core has a composition of:

wherein x=y+y'+y"; provided that x is less than or equal to 0.5; 0.5>y≧0.1; 0.3≧y'≧0, 0.1≧y"≧0; A is any of, or a combination of Fe, Ca, and K; 0.1>a≧0; and 1.5≧z≧0.5.

In another embodiment, the glass core has a composition of:

wherein x=y+y'+y"; y=0.175; y'=0.2; and y"=0.007; a=0.025; A is any of, or a combination of Fe, Ca, and K; and 1.5≧z≧0.5.

Suitable glass cores may be obtained from commercial suppliers such as MO-SCI Specialty Products, LLC. (a subsidiary of MO-SCI Corporation, Rolla, Mo.).

Nanoparticle Composite Coating

The nanoparticle composite coating comprises a nanoparticle colloidal component in combination with a binder derived from an alkoxide. The nanoparticle composite coating is a skeletal framework of oxides and oxyhydroxides derived from the hydrolysis and condensation of alkoxides and other reagents combined with the larger structure introduced by the colloidal oxide, which creates a porous layer surrounding the glass core. The scaffold material comprises combinations of the colloidal oxides with oxides and oxyhydroxides, or their mixtures, of aluminum, silicon, niobium, tantalum, titanium, and niobium. For use in resonant light scattering assays, the nanoparticle composite coating has a thickness of less than 700 nanometers, preferably, from about 1 nanometer to about 600 nanometers. The thickness of the coating may be determined using methods known in the art, such as scanning electron microscopy.

The nanoparticle composite coating may be comprised of any combination of colloidal particles, ranging in size from about 2 nanometers to about 100 nanometers. Suitable colloidal nanoparticles include, but are not limited to, colloidal oxides of elements such as silicon, zirconium, titanium, aluminum, cerium, antimony, and any combination thereof. The porosity of the nanoparticle composite coating may be tuned by appropriate choice of size or size distribution of the colloidal oxides.

Suitable colloidal oxides are commercially available, for example, from Nalco Chemical Company (Napperville, Ill.) or Nyacol Nano Technologies, Inc. (Ashland, Mass.). Additionally, colloidal oxides may be prepared using methods known in the art (see for example, *Inorganic Colloid Chemistry*, volumes 1, 2 and 3, J. Wiley and Son, Inc., New York, N.Y., 1935). Colloid formation involves either nucleation and growth or subdivision or dispersion processes. For example, hydrous titanium dioxide colloids may be prepared by adding ammonium hydroxide to a solution of tetravalent titanium salt, followed by peptization (re-dispersion) by dilute alkalis. Zirconium oxide colloids may be prepared by dialysis of sodium oxychlorides. Cerium oxide sol may be prepared by dialysis of a solution of ceric ammonium nitrate.

The inorganic metal alkoxides used as starting material in combination with the colloidal nanoparticles for preparing the microspheres of the invention may include any alkoxide which contains from 1 to 20 carbon atoms, and preferably from 1 to 5 carbon atoms in the alkoxide group. Suitable inorganic metal oxides include, but not limited to, aluminum tri-sec butoxide, tetraethylorthoxisilicate, niobium ethoxide, tantalum ethoxide, zirconium n-propoxide, and titanium ethoxide. Alkoxides having one to four carbon atoms, such as titanium ethoxide, and aluminum trisecondary butoxide, are preferred. Additionally, inorganic metal alkoxides that are soluble in the liquid reaction medium are preferred. Suitable inorganic metal alkoxides are available commercially. For example, commercially available alkoxides, such as tetraethylorthosilicate and Tyzor™ organic titanate esters may be used. Additionally, inorganic alkoxides may be prepared by various routes, such as for example, direct reaction of zero valent metals with alcohols in the presence of a suitable catalyst; and the reaction of metal halides with alcohols. Alkoxy derivatives may be synthesized by the reaction of the alkoxide with alcohol in a ligand interchange reaction. Direct reactions of metal dialkamides with alcohol also form alkoxide derivatives. Additional examples are disclosed by Bradley et al. (*Metal Alkoxides*, Academic Press, New York, N.Y., 1978).

The process to form the nanoparticle composite coating on the lass core is carried out in a liquid medium. Generally, the liquid medium utilized in the process should be a solvent for the inorganic alkoxide or alkoxides used. Alkoxides that are reactive to water at room temperature need to be dispersed in a non-aqueous solvent, while alkoxides that are less reactive to water. (e.g., tetraethylorthosilicate) may be dispersed in water. The addition of acidic or basic reagents to the liquid medium can have an effect on the kinetics of the hydrolysis and condensation reactions, and the microstructure of the oxide/hydroxide binder derived from the alkoxide precursor. Generally, a pH range of 1-12 may be used, while a pH range of 1-6 preferred.

The glass core may be optionally treated with water, acid or base to initiate hydrolysis and condensation reactions of the alkoxides. In some cases, the glass core may be reacted with the alkoxides without added water, since the surface of the glass core contains hydroxyl groups and some nascent adsorbed water for the formation of the binder phase.

The glass core, the colloidal nanoparticles, and the inorganic metal alkoxide are added to the liquid medium and the mixture is refluxed under nitrogen for about 15 minutes to about 8 hours. The resulting nanoparticle composite-coated microspheres may be recovered using any means known in the art, such as filtration, centrifugation, or decantation. The microspheres may be rinsed with a nonaqueous solvent and subsequently rinsed with water.

In general, the thickness and porosity of a coating layer may be controlled by the relative proportions of the colloidal components and the alkoxide reagent precursors. For the silicon oxide system (e.g., colloidal silicon oxide combined with tetraethyoxyorthosilane), a molar ratio (colloidal $SiO_2$/alkoxide derived $SiO_2$) of about 1 yields a coating thickness of about 400 to 600 nanometers. Lowering this ratio to 0.1 or below will result in a coating layer thickness of less than 200 nanometers. A preferred range of the molar ratio for use in the invention is 0.1 to about 3, more preferably, about 0.5 to about 2. Additionally, the thickness of the coating may be controlled by repeated sequential depositions of the coating layers, provided that the underlying layer is not disturbed.

Additionally, the microspheres comprising the nanoparticle composite coating may be optionally heat-treated at elevated temperatures to further modify the properties of the nanoparticle composite coating and to help further anchor the coating to the surface of the glass core. Typically, a temperature of about 100° C. to about 600° C. may be used for the heat treatment step, depending on the melting point of the glass core. Specifically, a temperature that would melt the glass core is not desired. The atmosphere used for the heat treatment may be non-oxidizing (for example nitrogen or argon) or the treatment may be done in air.

Microspheres Comprising a Bioactive Probe

The microsphere of the invention is prepared by applying a capture probe that is bioactive to the surface of the nanoparticle composite-coated glass core. The capture probe may be any chemical or biological structure or moiety, including, but not limited to, protein, polypeptide, polynucleotide, antibody or antibody fragment, biological cells, microorganisms, cellular organelles, cell membrane fragments, bacteriophage, bacteriophage fragments, whole viruses, viral fragments, organic ligand, organometallic ligand, and the like that may be used to bind either non-specifically to multiple analytes, or preferentially, to a specific analyte or group of analytes in a sample.

The probe may be applied to the surface of the nanoparticle composite-coated microspheres by either directly synthesizing the probe on the surface or by attaching a probe that is naturally occurring or has been synthesized, produced, or isolated separately to the surface using methods know in the art, as described by Prober et al. in copending and commonly owned U.S. Patent Application Publication No. 2005/0019842, which is incorporated herein by reference. The utility of the invention is enhanced by using a set of microspheres, each of which has one or more unique capture probes exposed on its surface. Such a set may be generally referred to as a "library" of microspheres or probes.

Microspheres comprising a bioactive probe may be prepared by derivatizing the surface of the nanoparticle composite-coated microspheres such that the appropriate capture probes may be attached using linker chemistries or crosslinking chemistries, which are well known in the art. Examples of linking groups include, but are not limited to, hydroxyl groups, amino groups, carboxyl groups, aldehydes, amides, and sulfur-containing groups such as sulfonates and sulfates. Examples of crosslinking chemistries include, but are not limited to, hydroxy reactive groups such as s-triazines and bis-epoxides, sulfhydryl reactive groups such as maleimides and haloacetyl derivatives, amine reactive groups such as isothiocyanates, succinimidyl esters and sulfonyl halides and carboxyl reactive groups such as carbodiimides.

One class of capture probes comprises proteins. By "protein" is meant two or more covalently linked amino acids; thus the terms "peptide", "polypeptide", "oligopeptide", and terms of similar usage in the art are all to be interpreted synonymously in this disclosure. Libraries of protein capture probes may be prepared, for example, from plant or animal cellular extracts, using the linker chemistries described above to attach the protein to the surface of the nanoparticle composite-coated microspheres. Particularly useful and thus preferred are libraries of human proteins, for example human antibodies.

Another class of capture probes comprise nucleic acids or nucleic acid mimics, such as peptide nucleic acids (PNA), which may also be known as "DNA fragments", "RNA fragments", "polynucleotides", "oligonucleotides", "gene probes", "DNA probes" and similar terms used in the art, which are all to be considered synonymous in the present disclosure. Methods for preparing nucleic acid probes or pseudo-nucleic acid probes, such as PNA, are well known in the art. For example, the nucleic acid probes may be prepared using standard β-cyanoethyl phosphoramidite coupling chemistry on controlled pore glass supports using commercially available DNA oligonucleotide synthesizers, such as that available from Applied Biosystems (Foster City, Calif.). The synthesized nucleic acid probes may then be coupled to the nanoparticle composite-coated microspheres using covalent or non-covalent coupling, as is well known in the art. Surface preparation of the nanoparticle composite-coated glass microspheres useful for this invention may include, for example, linker chemistry, affinity capture by hybridization or by biotin/avidin affinity, combinatorial chemistry, and others known in the art.

In another approach, the capture probe may be directly synthesized on the surface of the nanoparticle composite-coated microspheres of the invention. Probes that may be directly synthesized on the nanoparticle composite-coated microspheres include, but are not limited to, nucleic acids (DNA or RNA), peptide nucleic acids, polypeptides and molecular hybrids thereof. In the direct synthesis approach, a microsphere that is derivatized with a reactive residue to be used to chemically or biochemically synthesize the probe directly on the microsphere is used. The chemical linkage of the reactive residue must not be cleavable from the micropar­ticle during post-synthesis deprotection and cleanup of the final microspheres (Lohrmann et al., *DNA* 3, 1222 (1984); Kadonaga, J. T., *Methods of Enzymology* 208, 10-23 (1991); Larson et al., *Nucleic Acid Research* 120, 3525 (1992); Andreadis et al. *Nucleic Acid Res.* 228, e5 (2000); and Chri­sey et al. WO/0146471). This approach allows for mass production and assembly of libraries.

In some applications, e.g., assays in complex biological fluids such as urine, cerebrospinal fluid, serum, plasma, and the like, it may be necessary to treat the nanoparticle composite-coated microspheres to prevent or reduce non-specific binding of sample matrix components. Methods to reduce non-specific binding to a variety of solid supports in heterogeneous assays are well known in the art and include, but are not limited to, treatment with proteins such as bovine serum albumin (BSA), casein, and non-fat milk. These treatments are generally done after the attachment of the capture probe to the microspheres, but before the assay to block potential non-specific binding sites. Additionally, surfaces that resist non-specific binding can be formed by coating the surface with a thin film comprising synthetic polymers, naturally occurring polymers, or self-assembled monolayers that consist of a single component or a mixture of components. The thin film may be modified with adsorption-repelling moieties to further reduce non-specific binding. For example, the thin film may be a hydrophilic polymer such as polyethylene glycol, polyethylene oxide, dextran, or polysaccharides, as well as self-assembled monolayers with end functional groups that are hydrophilic, contain hydrogen-bond acceptors but not hydrogen bond donors, and are overall electrically neutral (Ostuni, E. et al., "A Survey of Structure-Property Relationships of Surfaces that Resist the Adsorption of Protein", Langmuir, 17, 5605-5620, (2001)). In this approach, the non-specific binding resistant layer is generally formed on the microsphere and then is chemically activated to allow attachment of the capture probe.

Analyte Detection Using Resonant Light Scattering

Assays carried out with the microspheres of the present invention may make use of the specific interaction of binding pairs, one member of the pair located on the surface of the microsphere (also referred to as the "probe", "binding part­ner", "receptor", or grammatically similar terms) and the other member of the pair located in the sample (referred to as the "target", "analyte", or grammatically similar terms). Generally the analyte carries at least one so-called "determinant"

or "epitopic" site, which is unique to the analyte and has enhanced binding affinity for a complementary probe site.

The nature of assay types possible with the microspheres of the invention varies considerably. Probe/target binding pairs may, for example, be selected from any of the following combinations, in which either member of the pair may be the probe and the other the analyte: antigen and specific antibody; antigen and specific antibody fragment; folic acid and folate binding protein; vitamin B12 and intrinsic factor; Protein A and antibody; Protein G and antibody; polynucleotide and complementary polynucleotide; peptide nucleic acid and complementary polynucleotide; hormone and hormone receptor; polynucleotide and polynucleotide binding protein; hapten and anti-hapten; lectin and specific carbohydrate; enzyme and cofactor; enzyme and substrate; enzyme and inhibitor; biotin and avidin or streptavidin; and hybrids thereof, and others as known in the art. Binding pairs may also include members that form covalent bonds, such as, sulfhydryl reactive groups such as maleimides and haloacetyl derivatives, and amine reactive groups such as isothiocyanates, succinimidyl esters, sulfonyl halides, and carbodiimide reactive groups such as carboxyl and amino groups.

Specific examples of binding assays include those for naturally occurring targets, for example, antibodies, antigens, enzymes, immunoglobulin (Fab) fragments, lectins, various proteins found on the surface of cells, haptens, whole cells, cellular fragments, organelles, bacteriophage, phage proteins, viral proteins, viral particles and the like. These may include allergens, pollutants, naturally occurring hormones, growth factors, naturally occurring drugs, synthetic drugs, oligonucleotides, amino acids, oligopeptides, chemical intermediates, and the like. Practical applications for such assays include for example, monitoring health status, detection of drugs of abuse, pregnancy and pre-natal testing, donor matching for transplantation, therapeutic dosage monitoring, detection of disease, e.g. cancer antigens, pathogens, sensors for biodefense, medical and non-medical diagnostic tests, and similar applications known in the art.

Assays using the microspheres of the invention may be done using various specific resonant light scattering protocols and instrumentation as described by Prober et al., supra. For example, analyte binding to a microsphere may be detected and the amount of analyte in the sample may be determined. In general, when determining binding of an analyte by resonant light scattering methods, at least two measurements are made, one before exposing the particles to the analyte to establish a baseline, and one after exposing the particles to the analyte. The determination of binding is done by comparing the two spectra and is thus typically a "differential" measurement. Specifically, to detect binding of an analyte to a capture probe, at least one capture probe is applied to the nanoparticle composite-coated microspheres of the invention. The microspheres are optionally scanned, (i.e., irradiated with light of varying wavelength, over an analytical wavelength range within an optical wavelength range) one or more times over the analytical wavelength range to produce at least one first reference resonant scattering spectrum for each particle. The microspheres are scanned using a light scanning source such as a scanning diode laser or tunable dye laser. In principle, any optical wavelength range is applicable for the measurements of this invention. Preferably, the optical wavelength range is from about 275 to about 1900 nanometers, more preferably from about 600 to about 1650 nanometers. Preferably, the analytical wavelength range has a span of about 1 nanometers to about 20 nanometers, more preferably about 10 nanometers in width. More preferably the analytical wavelength range has a span of 10 nanometers from about 770 to about 780 nanometers.

The microspheres are then contacted with a sample suspected of containing an analyte. The microspheres are then scanned over the analytical wavelength range using the light scanning source one or more times to produce at least one second binding resonant light scattering spectrum for each particle. Detection of analyte binding is done by comparing either any one of the second binding resonant light scattering spectra to any one of the first reference resonant light scattering spectra, preferably the one most recently obtained, or any one of the second binding resonant light scattering spectra with a previous second binding resonant light scattering spectrum in the series. The amount of analyte in the sample may be determined by comparing the differences between the two compared resonant light scattering spectra, specifically, the degree of shift of one or more of the spectral features in the scattering spectrum observed upon binding. The amount of analyte in the sample may then be determined from a calibration curve prepared using known standards, as is well known in the art.

The microspheres of the invention may also be used for particle identification, a combination of particle identification and detection of binding, identification of analytes, and detection of analyte dissociation, as described by Prober et al., supra.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations used is as follows: "min" means minute(s), "h" means hour(s), "µL" means microliter(s), "mL" means milliliter(s), "L" means liter(s), "nm" means nanometer(s), "mm" means millimeter(s), "cm" means centimeter(s), "µm" means micrometer(s), "pm" means picometer(s), "mM" means millimolar, "M" means molar, "mmol" means millimole(s), "µmole" means micromole(s), "g" means gram(s), "µg" means microgram(s), "mg" means milligram(s), "g" means the gravitation constant, "rpm" means revolutions per minute.

Example 1

Microspheres having a Borosilicate Glass Core and a Nanoparticle Composite Silicon Oxide Coating Comprising a Bioactive Probe The purpose of this Example was to prepare microspheres having a borosilicate glass core and a nanoparticle composite silicon oxide coating comprising a bioactive probe. Borosilicate glass microbeads were coated with a nanoparticle composite coating formed by reacting colloidal silicon oxide with tetraethoxylorthosilane. The bioactive probe biotin was then coupled to the nanocomposite silicon oxide-coated microspheres.

Preparation of Nanocomposite Silicon Oxide-Coated Glass Microspheres:

Borosilicate microbeads having the composition expressed by the formula:

$$(Si_{1-x}B_yAl_{y'}Na_{y''}O_{(2-2x+3/2y+3/2y'+1/2y'')})_{1-a}(AO_2)_a$$

wherein x=y+y'+y''; y=0.213; y'=0.0258; and y''=0.035; a=0.002; A is any of, or a combination of Fe, Ca, and K; and $1.5 \geq z \geq 0$, were obtained from MO-SCI Specialty Products, LLC. (a subsidiary of MO-SCI Corporation, Rolla, Mo.). The microbeads were sieved between minus 25 and plus 20 μm screens by the supplier.

The microbeads (25 g) were added to a 1-L round-bottom flask equipped with a dropping funnel. The round-bottom flask assembly was purged with nitrogen for one hour. Then, 170 g of tetraethoxylorthosilane (Aldrich, Milwaukee, Wis.) and 170 grams of colloidal silicon oxide solution (HS-30, 30 wt % in water; Nyacol Products, Ashland, Mass.) were added to the flask. The mixture was refluxed for 2 h, after which the product was filtered and rinsed with alcohol and water. The product was screened on 20 to 25 mesh screens prior to attachment of the bioactive probe.

The thickness of the nanoparticle composite silicon oxide coating was determined to be approximately 400 to 600 nm from fracture scanning electron microscopy images.

Preparation of Biotinylated Nanocomposite Silicon Oxide-Coated Glass Microspheres:

A mixture of about 1 g of the nanocomposite silicon oxide-coated microspheres, 1.0 mL of 3-aminopropyltrimethoxysilane (APS), 300 μL of pyridine, and 25 mL of dry toluene in a 50-mL flask was gently refluxed under nitrogen overnight (16-18 h). After cooling, the liquid layer was decanted and the residual microspheres were washed 3 times with 10 mL portions of dry toluene. The microspheres were cured at 100° C. overnight (16-18 h) under nitrogen. The cured microspheres were stored under nitrogen at room temperature.

The APS treated microspheres (100 mg) were combined with 200 μL of a 50 mM solution of Sulfo-NHS-SS-Biotin (Pierce Biotechnology, Rockford, Ill., Cat #21331) in 400 μL of 25% DMF/0.1 M sodium bicarbonate, pH 8.3. The resulting suspension was mixed at room temperature overnight on a rotating platform. Then, the microspheres were washed multiple times with 0.1 M sodium phosphate buffer, pH 7.4 and water, and then centrifuged at 13,000 rpm for 5 min into a Centricon® Centrifugal Filter Unit, YM-100 (Millipore Corp, Billerica, Mass.). The microspheres were stored dry at 4° C. until further use.

Examples 2 and 3

The purpose of these Examples was to demonstrate the improved sensitivity obtained with borosilicate microbeads having a nanocomposite silicon oxide coating compared to the uncoated microbeads in a bioassay using resonance light scattering detection.

The resonant light scattering of the biotinylated-nanocomposite silicon oxide-coated microspheres was measured using the method and instrumentation described below.

Figure 1:
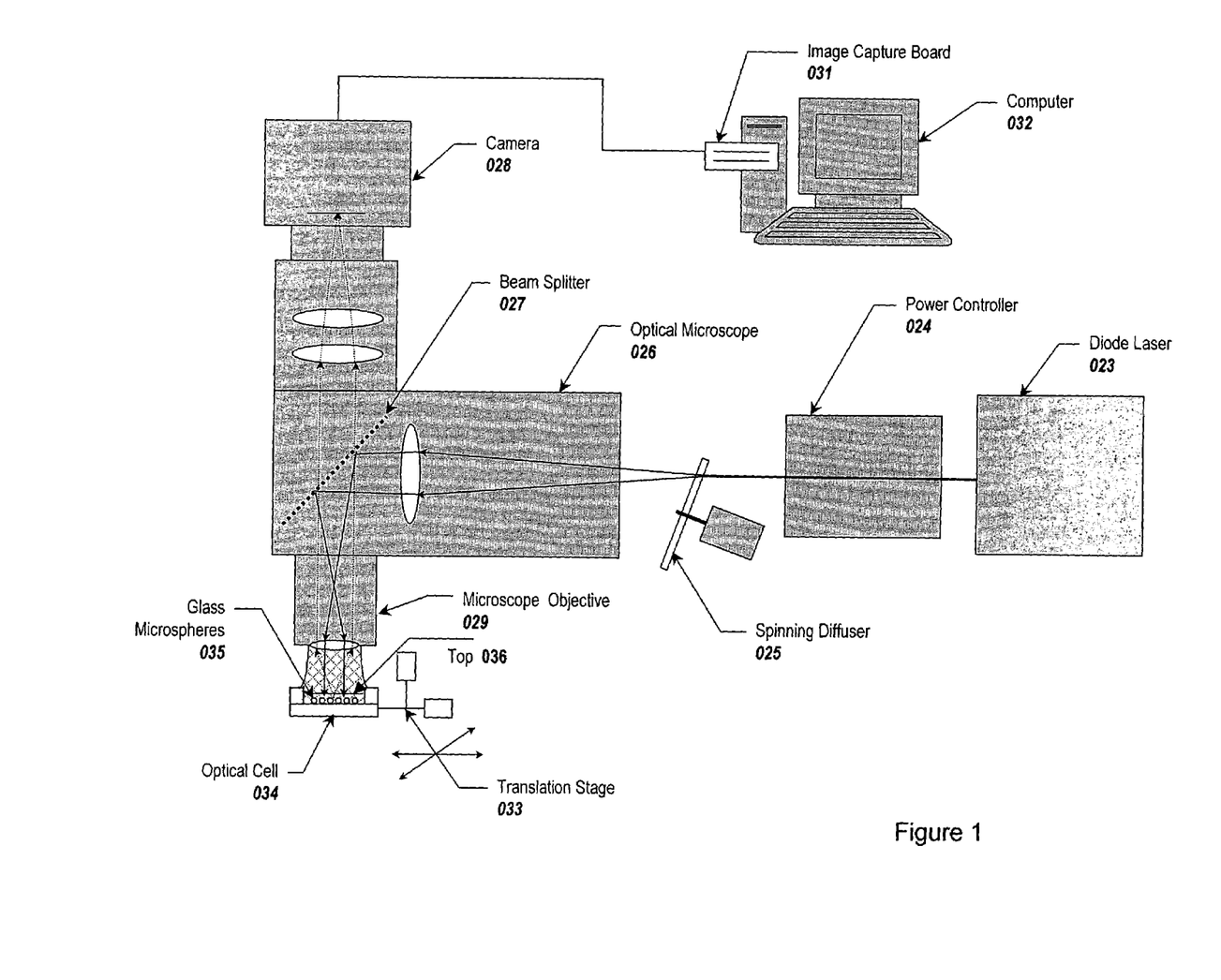
FIG. 1 is a schematic diagram of the imaging detection system used to measure resonant light scattering from microspheres, as described in Examples 2 and 3.

Five milliliters of PBS buffer (Sigma-Aldrich, St. Louis, Mo., Cat #3813,) was flushed through a closed-top optical cell (034), [cell cover shown as 036] shown in FIG. 1, which contained a micro-machined silicon substrate containing inverted pyramidal pits to stabilize the position of the microspheres. Approximately 1 μL of the biotinylated-nanocomposite silicon oxide-coated microspheres, prepared as described in Example 1, (dry) were placed into 200 μL of PBS buffer and gently agitated. Then, 1 μL of the microsphere suspension (035) was pipetted onto the silicon substrate in the cell and the cell was closed. The cell was placed on a translation stage (033) in the detection apparatus, as shown in FIG. 1. The microspheres were manipulated by flowing PBS solution through the cell. The microspheres that remained in place were scanned three times using the detection system, described below.

Figure 2:
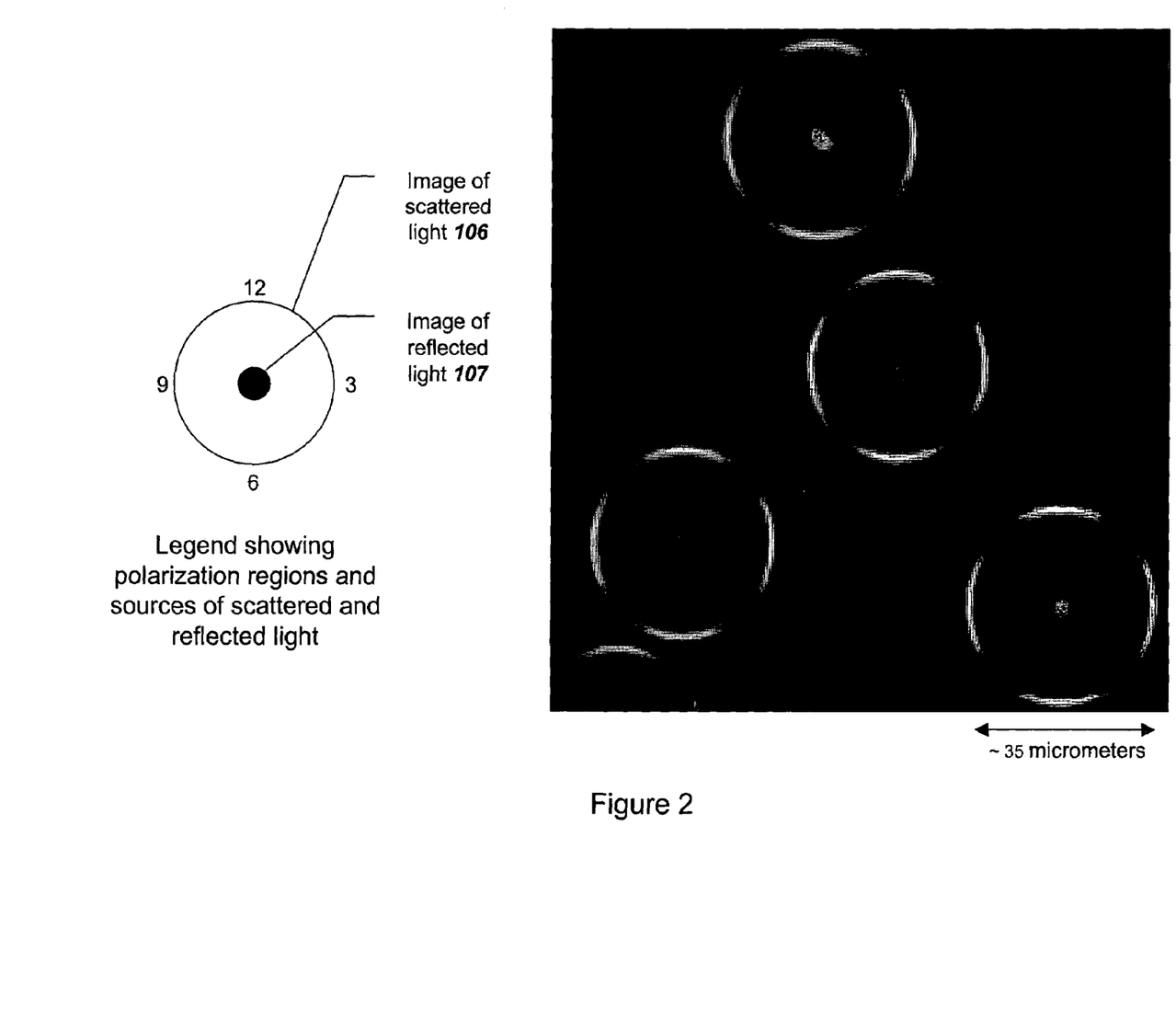
FIG. 2 is a digital image of scattered light from a group of microparticles, at a single wavelength of incident light. Both the incident and scattered light were polarized; the directions of the polarization were parallel. The numbers 12, 3, 6, and 9 refer to regions of the scattered light image for each particle as explained in Examples 2 and 3.

The microscope (026) (Model U-KMAS, Olympus Industrial) was set up for bright field illumination using a diode laser (023) (Model Velocity 6312, New Focus, Inc.), operating at constant current, as the light source. The output of the laser passed through an electro-optic power controller (024) (Model MI-10450-NIR, Brockton Electro-Optics) which was used to flatten the gain structure of the laser output and control the power of the laser radiation delivered to the microscope. Upon exiting the power controller the laser beam passed through a holographic diffuser (025) (Model LSD5GL3-2.75/0.25, Physical Optics) spinning at 1800 rpm. This spinning diffuser serves to eliminate the laser speckle pattern in the illumination field, which would otherwise interfere with the acquisition and analysis of image data. The standard beam splitter installed by the microscope manufacturer was replaced by a pellicle-type beam splitter (027) (National Photocolor) in order to eliminate interference fringes in the image. To acquire scattering spectra from a multiplicity of particles simultaneously, a set of particles was first placed in the field of view of the microscope and focused with the objective lens (029) (Model UMPLFL 20XW, Olympus Industrial). Once the particles of interest were in the field of view and focused, the laser was scanned in wavelength, typically from 780 to 770 nm in 20 s. During this scan, the digital camera (028) (Model KP-F120CL-S5-R2, Hitachi Instruments) acquired a complete scattered light image of the field of view at each wavelength. Each image was captured by an image capture board (031) (PCI-1428, National Instruments) installed in a personal computer (032) (Dell Precision 370 Workstation). Custom software was written to store each image. A wavelength scan resulted in a set of linked images, one for each wavelength in the scan. A typical Image is shown in FIG. 2. To determine the scattering spectrum of each particle in the field of view from a set of wavelength-linked Images, software was written to identify a representative region or regions of the image corresponding to each particle. For example, a portion of the ring-shaped scattered light image (106) surrounding the bright spot of reflected light (107) at each particle center as seen in the image of FIG. 2. In this Example, the incident and scattered light beams were polarized independently, with the two axes of polarization parallel to each other. This resulted in sectors of scattered light centered approximately at the 12:00, 3:00, 6:00, and 9:00 positions of the circle as indicated for the center image of FIG. 2 by the numbers 12, 3, 6, and 9 respectively. Theory predicts, and results confirm, that scattered light spectra from the "12" and "6" regions are equivalent and scattered light spectra from the "3" and "9" regions are equivalent. Furthermore, spectra from the two pairs of sectors are different from one another.

After three wavelength scans, the PBS was replaced with 2500 μL of a 2×SSC buffer, which was prepared by dilution of a 20× stock SSC Buffer (Sigma-Aldrich, St. Louis, Mo., Cat #S-6639), at a flow rate of 16 μL/s and 3 wavelength scans were performed as described above. The refractive index of the 2×SSC buffer was measured on an ARIAS 500 refractometer (Reichert Analytical Instruments, Depew, N.Y.) and was found to be 1.33788. The 2×SSC buffer served as a control for the resonant light scattering measurements. The 2×SSC buffer in the optical cell was replaced with 2500 μL of PBS buffer and 3 wavelength scans were taken. A 2500 μL solution of streptavidin (Pierce Biotechnology, Cat 21125) in PBS (50 μg/mL) was injected into the optical cell at a flow rate μL/s. At the end of the injection, 3 wavelength scans were taken. The microspheres were washed with 2500 μL of PBS at a flow rate of 16 μL/s to remove the unbound streptavidin and then three more wavelength scans were obtained.

The resonance light scattering spectra of the prescan, refractive index scan and the final scans were auto-analyzed using custom software. The auto-annulus software performed an image intensity thresholding of the pixels obtained in a 60-degree arc and computed each of the values per wavelength. The values calculated are combined to form a spectrum for each particle measured under each experimental condition. The resultant spectral shift between the pre and post scans was calculated using custom software. The mean shift values obtained upon streptavidin binding for 8 microspheres are given in Table 1.

For comparison, borosilicate microspheres having the same composition but not having the nanocomposite silicon oxide coating were biotinylated as described above. These microspheres were tested using the resonance light scattering method described above. The mean shift values obtained upon streptavidin binding for 16 microspheres are given in Table 1.

TABLE 1

Resonance Light Scattering Shift Values Obtained Upon Streptavidin Binding to Biotinylated Glass Microspheres

| Example | Glass Microspheres | Median Shift 2 × SSC pm | Mean Shift Streptavidin pm | Standard Deviation pm |
|---|---|---|---|---|
| 2 | silicon oxide coated | 284 | 507 | 170 |
| 3, Comparative | No silicon oxide coating | 295 | 296 | 47 |

As can be seen from the data in the Table, the biotinylated, nanocomposite silicon oxide coated-microspheres gave a significantly larger shift than the biotinylated, uncoated microspheres upon exposure to streptavidin (i.e., a 71% shift increase). The shifts obtained upon exposure to the control 2×SSC solution were comparable for both types of particles, indicating that the particles gave essentially equivalent shifts due to the refractive index change produced by the 2×SSC solution. This result suggests that the enhanced shift obtained with the biotinylated, nanocomposite silicon oxide coated-microspheres was due to the silicon oxide coating, and not to any inherent difference in the resonance light scattering properties of the borosilicate glass microspheres used.

What is claimed is:

1. A microsphere for use in a bioassay comprising a glass core coated with a nanoparticle composite coating comprising a bioactive probe, wherein the nanoparticle composite coating comprises:
   a) a colloidal oxide of an element selected from the group consisting of silicon, zirconium, aluminum, titanium, cerium, antimony, and mixtures thereof, wherein the colloidal oxide has a particle size of about 2 nanometers to about 100 nanometers; and
   b) a non-colloidal oxide or oxyhydroxide of an element selected from the group consisting of silicon, zirconium, aluminum, titanium, tantalum, niobium, and mixtures thereof.

2. A microsphere according to claim 1 wherein the bioactive probe is selected from the group consisting of proteins, polypeptides, polynucleotides, antibodies, antibody fragments, biological cells, microorganisms, cellular organelles, cell membrane fragments, bacteriophages, bacteriophage fragments, whole viruses, and viral fragments.

3. A microsphere according to claim 1 wherein the bioactive probe is synthesized on the surface of the coated microsphere.

4. A microsphere according to claim 1 wherein the bioactive probe is isolated from natural sources or synthesized separately prior to being attached to the surface of the coated microsphere.

5. A microsphere according to claim 4 wherein the bioactive probe is attached to the coated microsphere using linker chemistries or crosslinking chemistries.

6. A microsphere according to claim 5 wherein the linker chemistries employ linker groups selected from the group consisting of hydroxyl, amino, carboxyl, aldehyde, amide, sulfonate, and sulfate.

7. A microsphere according to claim 5 wherein the crosslinking chemistries employ reactive groups selected from the group consisting of s-triazines, epoxides, maleamides, haloacetyl derivatives, isothiocyanates, succinimidyl esters, sulfonyl halides, and carbodiimides.

8. A microsphere according to claim 1 wherein the bioactive probe is one member of a binding pair.

9. A microsphere according to claim 8 wherein the one member of a binding pair is selected from binding pair combinations consisting of: antigen/antibody, antigen/antibody fragment, Protein A/antibody, Protein G/antibody, hapten/anti-hapten, biotin/avidin, biotin/streptavidin, folic acid/folate binding protein; hormone/hormone receptor, lectin/carbohydrate, enzyme/cofactor, enzyme/substrate, enzyme/inhibitor, peptide nucleic acid/complimentary nucleic acid, polynucleotide/polynucleotide binding protein, vitamin B12/intrinsic factor; complementary nucleic acid segments; pairs comprising sulfhydryl reactive groups, pairs comprising carbodiimide reactive groups, and pairs comprising amine reactive groups.

10. A microsphere according to claim 1 wherein the glass core comprises a composition selected from the group consisting of:
   A) $[Ba_{1-x}Ti_y Si_{y'} B_{y''} Ca_{y'''} O_{(1-x+2y+2y'+3/2y''+y''')}]_{1-a}(AO_z)_a$, wherein $0.6 > y > 0.1$; $0.6 > y' > 0.05$; $0.6 > y'' \geq 0$; $0.4 > y''' \geq 0$; $x = y + y' + y'' + y'''$; A is any of, or a combination of Na, Fe, Sr, and Zr; $0.01 > a \geq 0$, and $2 \geq z \geq 0.5$;
   B) $[Ba_{1-x} La_y Si_{y'} Ti_{y''} B_{y'''} Ca_{y''''} O_{(1-x+3/2y+2y'+2y''+3/2y'''+2y'''')}]_{1-a}(AO_z)_a$; wherein $0.5 > y > 0.1$; $0.6 > y' > 0.05$; $0.6 > y'' > 0.04$; $0.4 > y''' \geq 0$; $0.3 \geq y'''' \geq 0$; $x = y + y' + y'' + y''' + y''''$; and wherein A is any of, or a combination of Cr, Fe, W, Na and Zr; $0.01 > a \geq 0$; and $3 \geq z \geq 0.5$; and
   C) a composition comprised of calcium, titanium, silicon and oxygen, wherein the calcium, titanium, and silicon content is given by:

$Ca_{1-x-y} Ti_x Si_y$ wherein x and y are independently equal to 0.2 to 0.5.

11. A microsphere according to claim 1 wherein the glass core comprises a silicon content of at least about 50 atom % and a composition selected from the group consisting of:
   A) $(Si_{1-x} B_y Al_{y'} Na_{y''} O_{(2-2x+3/2y+3/2y'+1/2y'')})_{1-a}(AO_z)_a$ wherein $x = y + y' + y''$, provided that x is less than or equal to 0.5, $0.5 > y \geq 0.1$; $0.1 \geq y' \geq 0$, $0.1 \geq y'' \geq 0$; A is any of, or a combination of Fe, Ca, and K; $0.1 > a \geq 0$; and $1.5 \geq z \geq 0.5$; and
   B) $(Si_{1-x} B_y Al_{y'} Na_{y''} O_{(2-2x+3/2y+3/2y'+1/2y'')})_{1-a}(AO_z)_a$ wherein $x = y + y' + y''$; provided that x is less than or equal to 0.5; 0.5>y≧0.1; 0.1≧y'≧0, 0.1≧y"≧0; A is any of, or a combination of Fe, Ca, and K; 0.1>a≧0; and 1.5≧z≧0.5.

12. A microsphere according to claim 11 wherein the glass core comprises a composition of:

$(Si_{1-x}B_yAl_{y'}Na_{y''}O_{(2-2x+3/2y+3/2y'+1/2y'')})_{1-a}(AO_z)_a$ wherein x=y+y'+y"; y=0.213; y'=0.0258; y"=0.035; a=0.002; A is any of, or a combination of Fe, Ca, and K; and 1.5≧z≧0.5.

13. A microsphere according to claim 1 wherein glass core has a diameter of about 10 micrometers to about 100 micrometers.

14. A microsphere according to claim 1, wherein the oxide or oxyhydroxide of (b) is aluminum tri-sec butoxide, tetraethylorthoxisilicate, niobium ethoxide, tantalum ethoxide, zirconium n-propoxide, or titanium ethoxide.

* * * * *